United States Patent [19]
Jablonski

[11] Patent Number: 5,976,501
[45] Date of Patent: *Nov. 2, 1999

[54] USE OF PRESSURE RESISTANT PROTEIN MICROSPHERES ENCAPSULATING GASES AS ULTRASONIC IMAGING AGENTS FOR VASCULAR PERFUSION

[75] Inventor: Edward G. Jablonski, Escondido, Calif.

[73] Assignee: Molecular Biosystems, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/665,028

[22] Filed: Jun. 7, 1996

[51] Int. Cl.⁶ ........................................................ A61B 8/13
[52] U.S. Cl. .............................................................. 424/9.52
[58] Field of Search ...................... 424/9.52; 128/662.02; 600/425, 58

[56] References Cited

U.S. PATENT DOCUMENTS

| | | | |
|---|---|---|---|
| 4,572,203 | 2/1986 | Feinstein | 424/9.52 |
| 4,844,882 | 7/1989 | Widder et al. | 424/9.52 |
| 4,957,656 | 9/1990 | Cerny et al. | 252/311 |
| 5,190,982 | 3/1993 | Erbel et al. | 521/56 |
| 5,393,524 | 2/1995 | Quay | 424/9 |
| 5,410,516 | 4/1995 | Uhlendorf et al. | 367/7 |
| 5,413,774 | 5/1995 | Schneider et al. | 424/9.51 |

FOREIGN PATENT DOCUMENTS

| | | |
|---|---|---|
| 0458745 | 9/1994 | European Pat. Off. . |
| 0633030 | 1/1995 | European Pat. Off. . |
| WO 92/05806 | 4/1992 | WIPO . |
| WO 92/17213 | 10/1992 | WIPO . |
| WO 94/08627 | 4/1994 | WIPO . |
| WO 94/16739 | 8/1994 | WIPO . |
| WO 95/23615 | 9/1995 | WIPO . |
| WO 96/04018 | 2/1996 | WIPO . |
| WO 96/09793 | 4/1996 | WIPO . |
| WO 96/15814 | 5/1996 | WIPO . |

OTHER PUBLICATIONS

Ophir et al., "Contrast agents in diagnostic ultrasound" *Ultrasound in Med. & Biol.* (1989) 15:319–333.

de Jong et al., "Quantification of transpulmonary echocontrast effects" *Ultrasound in Med. & Biol.* (1993) 19:279–288.

Schneider et al., "Polymeric microballoons as ultrasound contrast agents: Physical and ultrasonic properties compared with sonicated albumin" *Investigative Radiology* (1992) pp. 134–139.

Dittrich et al., "Reproducibility of myocardial opacification using FS069, a new intravenously administered ultrasound contrast agent" *JACC* (Feb. 1995) Abstract 955–55.

Xu et al., "Contrast echocardiographic assessment of myocardial perfusion following acute coronary artery occlusion and reperfusion using intravenous injection of aerosome™ MRX 115 in monkeys" *JACC* (Feb. 1995) Abstract 955–56.

(List continued on next page.)

*Primary Examiner*—Gary E. Hollinden
*Attorney, Agent, or Firm*—Morrison & Foerster LLP

[57] ABSTRACT

Conventional ultrasonic imaging methods are described which involve the use of aqueous suspension of microspheres. These microspheres are further characterized as consisting of gas cores encapsulated by a protein shell which are formed in the presence of perfluoroalkane vapors. The presence of the vapor during formation changes the shell characteristics and thus protects the gas from being solubilized in the surrounding aqueous environment. In addition, the presence of the perfluoroalkane vapor during formation may also provide improved echogenic properties for vascular imaging applications.

60 Claims, 6 Drawing Sheets

OTHER PUBLICATIONS

Porter et al., "Intravenous dextrose albumin sonicated with evaporated perfluoropentane reduces left ventricular cavity attenuation and improves the echocardiographic detection of posterior myocardial perfusion abnormalities" *JACC* (Feb. 1995) Abstract 955–57.

Church, "The effects of an elastic solid surface layer on the radial pulsations of gas bubbles" *J. Acoust. Soc. Am.* (1995) 97:1510–1521.

Dittrich et al., "Caridac ultrasound using second harmonics and intravenously administered albumin shell microspheres" *Am. Coll. Cardiol., 45th Annual Scientific Session* (1996) FS069 Bibliography with Abstracts (1 page total).

Figure 1

100% Air

50% Air and 50% Perfluoropropane

Figure 4

50% Air and 50% Perfluropentane Vapor

Figure 5

66.6% Air and 33.3% Perfluoropentane Vapor

Figure 6

Variable Air and Perfluoropentane Vapor

USE OF PRESSURE RESISTANT PROTEIN MICROSPHERES ENCAPSULATING GASES AS ULTRASONIC IMAGING AGENTS FOR VASCULAR PERFUSION

DESCRIPTION

1. Technical Field

The invention is in the field of methods of performing conventional grey-scale ultrasound imaging. More particularly, it concerns the use of ultrasound imaging agents comprising microspheres containing gas cores encapsulated by a shell of a biocompatible protein. The microspheres are rendered pressure resistant and efficacious by including a perfluoroalkane during microsphere formation. These microspheres are particularly well-suited for use as ultrasonic imaging agents to perfuse tissues and organs such as the myocardium to enhance visualization in a grey-scale image.

2. Background

Conventional ultrasonic imaging is based on the principle that waves of sound energy can be focused upon an area of interest and reflected in such a way as to produce an image thereof. The ultrasonic scanner utilized is placed on a body surface overlying the area to be imaged, and sound waves are directed toward that area. The scanner detects reflected sound waves and translates the data into video images. When ultrasonic energy is transmitted through a substance, the amount of energy reflected depends upon the velocity of the transmission and the acoustic properties of the substance. Changes in the substance's acoustic properties (e.g., variations in acoustic impedance) are most prominent at the interfaces of different acoustic densities, such as liquid-solid or liquid-gas. Consequently, when ultrasonic energy is directed through tissue, organ structures generate sound reflection signals for detection by the ultrasonic scanner. These signals can be intensified by the proper use of a contrast agent.

Ophir and Parker, Ultrasound in Medicine and Biology 15(4):319–333 (1989), describe various types of gas-containing ultrasonic contrast agents. One major class of gas-containing ultrasound contrast agents described by Ophir and Parker are the encapsulated gas microbubbles or microspheres. The gas bubble is surrounded by a shell composed of a protein or other biocompatible material. A current commercial microsphere contrast agent is ALBUNEX® (Molecular Biosystems, Inc., San Diego, Calif.) which is composed of human serum albumin encapsulated air microspheres. See U.S. Pat. Nos. 4,572,203 and 4,844,882. Air microspheres, however, have been shown to quickly lose echogenicity when subjected to pressures of 150 mm Hg, such as would be encountered during injection and circulation in vivo (deJong, N. et al., *Ultrasound Med. Biol.* 19:279–288, 1993).

In an effort to solve the pressure-instability problem, recent teachings have centered on improving the shell, because, it is believed, the microsphere shells or "membranes" are too fragile or brittle under pressure, resulting in rapid collapse in vivo. Giddey (PCT WO 92105806) stated, "because of their rigidity, the membranes can not sustain sudden pressure variations to which the microspheres can be subjected, for instance during travel through the bloodstream, these variations or pressure being due to heart pulsations." To overcome shell rigidity, he proposed to pre-emulsify air in a protein solution containing a large percentage of a viscosifying agent (40%–80% polyols) and subject it to mechanical shear in a high speed blender. Bubbles of the appropriate size are collected and coated with a suitable surfactant to stabilize them in a soft shell.

Holmes (PCT WO 92/17213) proposed to enhance the in vivo stability of protein microspheres by strengthening the shell with biodegradable chemical crosslinking reagents.

Bichon et al. (European Patent Application 458,745A1) and Schneider et al. (Inv. Radiol. 27:134–159, 1992) describe the production of porous (5 to 2000 nm pore size) polymeric "microballoons". They report in the European Patent Application that "the microporous structure of the microballoon's envelope is a factor of resiliency, i.e., the microspheres can readily accept pressure variation without breaking."

Erbel and Zotz (U.S. Pat. No. 5,190,982) describe a crosslinked polymeric microcapsule in which air is entrapped.

Other efforts to improve microsphere stability have concentrated on the gas inside the shell, and in particular have centered on the incorporation of insoluble gases. According to Henry's law, the solubility of a given gas in solution increases as pressure increases. When a bubble of gas in solution is subjected to pressure, the solubility of the gas in the surrounding solution will increase in proportion to the amount of pressure. If the bubble of gas is surrounded by a shell, i.e., in the form of a microsphere, the effects of gas solubility are still observed, since microsphere shells do not completely eliminate contact between gas in the microsphere and the surrounding solution. Hence, when microspheres suspended in solution are subjected to pressure, the gas inside the microspheres eventually becomes solubilized in the surrounding solution which results in collapse of the microspheres. The more insoluble the gas is in the surrounding solution, the more resistant the microspheres will be to becoming completely solubilized in the blood system or tissues.

U.S. Pat. No. 5,413,774 indicates that the pressure resistance of microspheres can be improved by having at least a portion of the gas that is encapsulated be a gas which has a $S_{gas}\sqrt{MW_{gas}} \leq 0.0031$, where $S_{gas}$ is the water solubility of the gas in liters/liter and $MW_{gas}$ is the average molecular weight of the gas in Daltons. Included in the gases suggested by this patent are the relatively insoluble perfluoroalkanes $CF_4$, $C_2F_6$, and $C_4F_{10}$.

PCT application WO 95/01187 describes microspheres of gas encapsulated by a heat-insolubilized filmogenic protein wherein the encapsulated gas is entirely a water insoluble gas. Among the gases specifically mentioned are the perfluoroalkanes $CF_4$, $C_2F_6$, $C_3F_8$, and $C_4F_{10}$. These microspheres are made by subjecting a mixture of an aqueous solution of the protein and the insoluble gas to ultrasonic or mechanical cavitation in the absence of oxygen by sonicating or milling the mixture in a sonicator/mill that is closed to the atmosphere.

Various other examples of insoluble gas-containing microspheres have been described which contain high boiling point perfluoroalkanes, such as perfluoropentane, as the core material. PCT WO 95/23615 describes microspheres that are made by mixing liquid perfluoropentane with the shell-forming material and subsequently converting it to a gas. PCT WO 96/04018 describes microspheres with fluorine-containing shells encapsulating insoluble gases, such as perfluoropentane. Porter, et al. (Journal of Amer. College of Cardiology, Abstract No. 955-57, February, 1995) describes dextrose albumin microspheres made with evaporated perfluoropentane.

Other patent literature describes non-microsphere-type ultrasound contrast agents that include high boiling-point perfluoroalkanes. U.S. Pat. No. 5,393,524 describes free gas microbubbles of various gases that exhibit increased pressure resistance relative to free air microbubbles. Perfluoropentane is among the numerous gases mentioned in Table IV of that application. PCT WO 94/16739 describes ultrasonic contrast agents that are liquid-liquid emulsions in which the dispersed liquid has a boiling point below physiological temperature. When the emulsion is administered, the dispersed liquid boils. Perfluoropentane is included in the list of compounds that may be used as the dispersed liquid.

The foregoing discussion relates to various contrast agents which are useful for conventional ultrasonic imaging which involves the formation of images from the amount of reflected ultrasonic signal. Recently, a different technique has been described for generating an ultrasonic image which involves detecting changes in the harmonic frequency of the reflected ultrasonic signal due to the resonance of the imaging agent. This technique, which is referred to as "harmonic imaging" is described by Uhlendorf, et al (U.S. Pat. No. 5,410,561). Because relatively solid objects resonate less upon application of ultrasonic energy, free microbubbles are better in harmonic imaging than encapsulated microspheres. PCT WO 96/09793 describes free microbubbles, stabilized by surfactants, that contain various gaseous material that undergo volume changes upon application of ultrasonic energy that result in enhanced harmonic imaging.

Although harmonic imaging may provide some improvements over conventional ultrasonic imaging for certain applications, conventional imaging is still preferred for practical reasons, since apparatuses capable of performing harmonic imaging are not widely available. Accordingly, it is an object of the present invention to provide for a method of imaging using microspheres which are specially adapted and useful for conventional ultrasonic imaging of tissues or organs.

The microspheres which are useful in the present invention contain a soluble, biocompatible gas such as air in a protein shell which are formed in the presence of a heated perfluoroalkane vapor. The perfluoroalkane interacts with the protein during formation to make the microsphere shell more impermeable to the aqueous environment and is also believed to play an important roll in shell formation which results in improved imaging efficacy. By including the heated perfluoroalkane vapor during microsphere formation, a relatively soluble gas, such as air, is unexpectedly protected from solubilization in the surrounding aqueous environment. Accordingly, the microspheres of the present invention exhibit pressure resistance beyond that expected for equivalent microsphere made in the absence of the perfluoroalkane. The result is an extremely long lived in vivo product capable of sustained echogenicity using conventional ultrasonic procedures.

DISCLOSURE OF THE INVENTION

The present invention provides a method of conventional ultrasound imaging using a suspension of microspheres as a contrast agent. The microspheres are prepared using a gas as a core material which is encapsulated by a heat-insolubilized protein shell formed in the presence of a heated perfluoroalkane vapor. The gas is preferably soluble. The vapor is preferably provided at a temperature above its boiling point, close to the denaturation temperature of the protein, which facilitates formation of the microsphere shells and results in enhanced ultrasonic efficacy. Ultrasonic imaging of a subject is commenced, then the microsphere suspension is administered to the subject. The microsphere suspension can be administered as either a bolus, or it can be administered continuously over a period of time. It is also contemplated that the microsphere suspension can be packaged in pre-filled syringes which are ready for use.

Imaging is continued while the microspheres reach the site of the tissues or organs being examined. Imaging is generally continued until the image intensity of the tissue or organ being examined has returned to pre-administration intensity. The ultrasonic images are generated from the reflected ultrasonic energy.

One aspect of the present invention is the use of the invention method for studying vascular perfusion of tissues and organs, which provides an assessment of blood flow through the tissues or organs. The invention method is particularly useful for studying myocardial perfusion. Myocardial imaging involves imaging the myocardium before administration of the microsphere suspension, administering the microsphere suspension, and continuing the imaging as the microspheres enter the left ventricular cavities, perfuse the myocardial tissue, exit the ventricular cavity, and eventually exit the myocardial tissue.

The method of imaging of the present invention can be performed using conventional two-dimensional or multi-dimensional (e.g. three-dimensional) ultrasound equipment. In addition, the method may be performed with either continuously applied or pulsed ultrasound.

Preferably, the microsphere suspension will contain microspheres in the range of $1 \times 10^7$ to $1 \times 10^{10}$ per mL of suspension. Further, the microspheres will preferably have a mean diameter in the range of 0.1 and 10 microns, more preferably 2 to 6 microns.

The microsphere core can consist of any gas which is biocompatible, with soluble gases such as air being preferred. The perfluoroalkane vapor can be the vapor form of a linear, branched or cyclic perfluoroalkane, with linear perfluoroalkanes such as perfluoropentane, perfluorohexane and perfluoroheptane being preferred. The amount of perfluoroalkane vapor delivered into the microsphere forming process relates to its molecular weight, with less perfluoroalkane vapor being required as the molecular weight increases. However, the gas phase (the gas and the perfluoroalkane vapor) should consist of at least 50% gas to avoid producing less efficacious negatively buoyant microspheres.

The shell-forming protein is heat-insolubilizable. Preferably, the shell-forming protein is albumin, and more preferably it is human serum albumin. Additionally, the shell may be modified to include moieties that render the microspheres less immunogenic and/or tissue or organ specific.

Another aspect of the present invention is a process for making microspheres which are useful in conventional ultrasonic imaging which involves mixing a gas phase consisting of a gas and a heated perfluoroalkane vapor with a solution of heat-insolubilizable protein under conditions which cavitate the mixture and heat insolubilize the protein to form microspheres, followed by cooling the microspheres to condense at least a portion of the perfluoroalkane into the shell. This step causes the perfluoroalkane to become associated with the shell's surface and/or inner structure to create a hydrophobic barrier. In addition, the acoustic properties of the shell are altered in the process, making a more efficacious microsphere.

The microspheres may be formed by cavitation using ultrasonic energy, or mechanical forces such as those produced in a colloid mill.

An additional aspect of the invention is compositions that are useful for conventional imaging consisting of microspheres having gas cores encapsulated by heat-insolubilized protein that are formed in the presence of heated perfluoroalkane vapors. The microspheres exhibit enhanced pressure resistance, such as resistance to a pressure of 10 psi. Other features of the microsphere compositions of the present invention are described in the foregoing discussion.

MODES FOR CARRYING OUT THE INVENTION

The microspheres which are useful with the method of the present invention consist of gas cores encapsulated by heat-insolubilized protein, and are formed in the presence of heated perfluoroalkane vapors. They are of a size suitable for transpulmonary passage, with a mean nominal diameter as measured with a Coulter Multisizer II particle counter/sizer (Coulter Electronics, Hialeah, Fla.) in the range of 0.1 to 10 microns, preferably 2 to 6 microns.

The exterior of the microsphere is defined by a thin protein shell. Protein shell material includes both naturally-occurring filmogenic proteins, proteins produced by recombinant DNA methodologies, and synthetic amino acid polymers, which herein are collectively referred to as "proteins." The protein must be able to form a shell or film about the core material when the protein is insolubilized. Suitable naturally-occurring proteins include albumin, gamma-globulin (human), apo-transferrin (human), J-lactoglobulin, urease and lysozyme. Particularly well suited for the present invention is albumin, and more particularly, human albumin.

Shell forming materials suitable for use in forming the microspheres, or the resulting microspheres, may be chemically modified for the purpose of organ/tissue targeting or quenching immunogenic activity (e.g., modification with antibodies or polyethylene glycol.)

Gases suitable for use in forming the microspheres within the present invention are preferably soluble, and pharmacologically acceptable, i.e., biocompatible and minimally toxic to humans. The term "biocompatible" means the ability of the gas to be metabolized without the formation of toxic by-products. The gas may be composed of a single compound or a mixture of compounds. Examples of gases suitable for use within the present invention are air, $O_2$, $N_2$, $H_2$, $CO_2$, $N_2O$; noble gases such as argon, helium, xenon; and hydrocarbon gases such as methane, ethane, propane, n-butane, isobutane and pentane. The term "soluble" means a gas having a solubility of greater than 0.01 mL of gas per mL of water at atmospheric pressure and a temperature of 25° C. Insoluble gases are also suitable for use, and include without limitation perfluoromethane, perfluoroethane, perfluoropropane, perfluorobutane and perfluoroisobutane, as well as mixtures of soluble gases and/or insoluble gases.

The microspheres which are useful in the present invention are further characterized as being formed in the presence of a heated perfluoroalkane vapor. The term "perfluoroalkane" intends a linear or branched chain hydrocarbon which is partially or totally fluorine-substituted, and may optionally contain other substituents, such as O, OH, S, NO, and the like. The perfluoroalkane will preferably have a relatively high boiling point, i.e. above 20° C. at standard pressure. Perfluoropropane, perfluorohexane and perfluoroheptane are preferred. The term "vapor" intends the gaseous phase of a liquid formed by raising the temperature of the liquid above its boiling point. The heated perfluoroalkane vapor interacts with the shell-forming protein during formation and subsequent cooling to render the resultant microsphere shell less permeable to the aqueous exterior. This helps to prevent contact between the internal gas core and the surrounding aqueous environment, which protects the gas from becoming solubilized in the aqueous environment, especially when the gas core comprises a soluble gas. The effects of loss of the gas core due to solubilization is observed as pressure instability. The microspheres of the present invention exhibit pressure resistance beyond that expected for an equivalent microsphere which is not formed in the presence of a heated perfluoroalkane vapor. Other hydrocarbons with similar properties to those described for perfluoroalkanes (i.e. boiling point, heat capacity, vapor density and molecular weight) are also within the present invention.

The microspheres are formed by first mixing the gas and the heated perfluoroalkane vapor (referred to herein collectively as the "gas phase"). This mixture is then maintained at an elevated temperature, preferably above the boiling point of the perfluoroalkane, and preferably near the thermal denaturation temperature of the shell-forming protein, until it is brought into contact with the protein solution in an appropriate microsphere-forming apparatus (usually a sonication chamber or a colloid mill). Alternatively, the gas and the heated perfluoroalkane vapor can be introduced separately. "Boiling point" intends the temperature at which the perfluoroalkane goes from the liquid phase to the vapor phase at a given pressure. When the perfluoroalkane is maintained at elevated pressures, this boiling point will necessarily be higher than it would be at 1 atm. Unless otherwise indicated, the term "boiling point" as used herein intends the boiling point at 1 atm.

Microspheres are formed by cavitation at a high enough temperature to sufficiently heat and insolubilize the shell-forming protein to encapsulate the gas phase. It is also important for the temperature during microsphere formation to be above the temperature at which the perfluoroalkane vapor would condense. After the microspheres are formed, subsequent cooling to below the boiling point of the perfluoroalkane vapor (29° C. for perfluoropentane, 60° C. for perfluorohexane and 80° C. for perfluoroheptane) after microsphere formation condenses at least a portion of the vapor into the shell protein to act as a hydrophobic barrier. This barrier may also include a liquid monolayer of perfluoroalkane at the gas-shell interface.

In addition to forming a hydrophobic barrier, the perfluoroalkane molecules are generally large relative to gas molecules, in particular molecules of low molecular weight soluble gases, and act to further isolate the core from the outside aqueous environment by occupying space within the shell and acting as a physical barrier to gas diffusion.

Additionally, the vapor of a high boiling point perfluoroalkane also has a high heat capacity relative to less dense gases, such as air. This property allows additional heat to be carried into the cavitation process by the vapor, enhancing the thermal denaturation of the surrounding protein. Accordingly, more protein molecules are incorporated into the shell during the shell-forming process due to the greater degree of local protein denaturation attributable to the presence of the heated perfluoroalkane vapor. These thicker or more dense protein shells result in superior properties in terms of echogenicity and in vivo stability, and also further serve to restrict exposure of the gas core to the surrounding medium.

Further, it is believed that the hydrophobic nature of, as well as the heat provided by, the perfluoroalkane vapor also allows shell material to be formed with new external properties, by directing the inward orientation of hydrophobic groups and the outward orientation of hydrophilic groups as the protein chain undergoes thermal denaturation and shell formation. This creates protein microspheres with the unexpected and defining property of interaction with the walls of the circulatory vessels of the myocardium and other organs. Gas-filled protein microspheres prepared in the presence of the heated vapor of the high boiling point perfluoroalkanes persist in the myocardium long after washing through the chamber of the heart when tested in vivo. Protein microspheres prepared with only gases do not persist in myocardial tissue after being eliminated from the left ventricle by cardiac output.

The introduction of too much perfluoroalkane additive increases the density of the individual microspheres, resulting in negatively buoyant particles, which settle out of suspension in 1% albumin in several hours. These negatively buoyant particles contain an excessive amount of liquid perfluoroalkane. The presence of too much liquid perfluoroalkane may result in microspheres of unstable, indeterminate and irregular size. Such negatively buoyant preparations of microspheres do not efficiently cross the lungs which filter out particles above 10 $\mu$m in diameter. Material which cannot cross the lungs is ineffective as an intravenous ultrasound contrast agent. Accordingly, the amount of perfluoroalkane vapor used in the process must be sufficient to enhance pressure stability without resulting in negative buoyancy.

The amount of perfluoroalkane to be introduced depends on its molecular weight. The higher the molecular weight, the less perfluoroalkane which can be introduced without forming negatively buoyant microspheres. Suitable amounts may be expressed as a volume per volume (v/v) percentage of the "gas phase" which is introduced, i.e., the total amount of gas plus perfluoroalkane vapor. For perfluoropentane, this amount is approximately 20–50%; for perfluorohexane, it is approximately 10–20%; and for perfluoroheptane, it is approximately 7–15%. Suitable amounts for other perfluoroalkanes can easily be determined on the basis of buoyancy and pressure resistance. It is also understood that the amount which is necessary is relatively independent of the chosen core gas.

The microspheres of the invention exhibit unexpectedly enhanced pressure resistance when the core is a soluble gas. If microspheres are prepared with 50% air and 50% of either perfluoropropane gas or perfluoropentane vapor (v/v) as the gas phase, these microspheres would be expected to exhibit the same resistance to a pressure of 10 psi for equivalent samples of approximately $1\times10^7$ microspheres per mL. This is because the solubility of air in the core, or diffusion through the shell, would not be expected to be diminished by the presence of the perfluoroalkane. Accordingly, microspheres made with the same amount of air would be expected to lose the air fraction after being subjected to sufficient pressure to solubilize only the air fraction, and suffer partial destruction. However, the microspheres of the present invention exhibit an unexpected resistance to pressure. Contrary to what would be expected, microspheres made with 50% air and 50% perfluoropentane vapor (v/v) exhibit almost complete resistance to 10 psi pressure. In contrast, microspheres prepared with 50% air and 50% perfluoropropane exhibit partial collapse due to loss of the air fraction. Microspheres prepared with perfluoropropane are resistant to 10 psi. See Example 2.

The microspheres are used in the form of a suspension in a sterile, aqueous, injectable vehicle. Such vehicles are well known in the pharmaceutical formulation art. The concentration of microspheres in the suspension will normally be in the range of $1\times10^7$ to $1\times10^{10}$, more usually $1\times10^8$ to $1\times10^9$, per mL of suspending medium. One percent human serum albumin in saline solution is a preferred vehicle. When in suspension, the microspheres are monodispersed and do not coalesce. The suspensions are preferably stored at 4°–23° C., pending use. Naturally, the microspheres may be kept in more concentrated or more dilute suspensions than specified above and then reformulated for injection.

The microspheres are made by subjecting a mixture of an aqueous solution of a heat-insolubilizable protein and the gas phase to ultrasound or mechanical cavitation at elevated temperatures, to cause the protein to simultaneously denature and encapsulate the gas phase, followed by cooling the product to 15–18° C. The concentration of protein in the solution is in the range of about 0.1 to 10% w/v, preferably about 1 to 5% w/v, and most preferably about 1% w/v. Mechanical cavitation is preferred, such as occurs in a colloid mill. Alternatively, mechanical cavitation may be brought about by forcing either the gas phase or the protein solution through aperatures of a size which is appropriate to make microspheres within a useful size range. Using mechanical cavitation in a colloid mill, the aqueous solution of the heat-insolubilizable protein is provided to the mill at a temperature necessary to achieve incipient denaturation temperature during the subsequent mechanical cavitation of the solution. The denaturation temperature of the protein in solution will normally be in the range of 50 to 100° C. It can be obtained from tables of thermal protein denaturation in the literature, or experimentally by any known method. For example, to determine the denaturation temperature experimentally, a protein solution can be heated in a water bath while stirring. The denaturation temperature is the temperature at which insoluble material is first observed. Note that the denaturation temperature is affected by the nature, purity and source of the protein, the concentration of protein in the solution, the pH, buffer, ionic strength, the presence of stabilizers and the presence of chemical denaturants or detergents. Therefore, it is necessary to determine the denaturation temperature of the protein in the environment in which it will be employed to make microspheres. If desired, additives such as detergents or polar solvents can be employed to change the temperature at which denaturation takes place.

The following table gives the denaturation temperatures of several naturally occurring proteins which were determined experimentally as described above:

TABLE 1

| PROTEIN | CONCEN-TRATION | pH | SOLVENT | $T_{denaturation}$ |
|---|---|---|---|---|
| Human Serum Albumin, USP Swiss Red Cross (Bern, Switzerland) | 50 mg/mL | 6.9 | 0.9% NaCl, 4 mM Sodium Caprylate, 4 mM Tryptophanate | 75° C. |
| Human Serum Albumin, USP Swiss Red Cross (Bern, Switzerland) | 10 mg/mL | 6.9 | 0.9% NaCl, 1 mM Sodium Caprylate, 1 mM Tryptophanate | 78° C. |
| J-Lactoglobulin, Sigma (St. Louis, MO) | 25 mg/mL | 7.6 | USP Water | 90° C. |
| IJ-Globin, Sigma (St. Louis, MO) | 25 mg/mL | 5.0 | USP Water | 90° C. |
| Lysozyme Sigma (St. Louis, MO) | 100 mg/mL | 7.5 | 5 mM TRIS*, 2 mM DTT*** | 31° C. as determined immediately after addition of DTT |
| Human Gamma Globulin, acid pH method, Sigma (St. Louis, MO) | 40 mg/mL | 5.0 | 10 mM MES**, pH 5.0 | 66° C. |
| Human Gamma Globulin, alkaline pH method, Sigma (St. Louis, MO) | 40 mg/mL | 9.8 | 10 mM TRIS, pH 9.8 | 69° C. |
| apo-Transferrin, Sigma (St. Louis, MO) | 20 mg/mL | 7.5 | 10 mM TRIS* | 71° C. |

*TRIS = 2-amino-2-(hydroxymethyl)-1,3-propanediol
**MES = 2-(N-morpholino)ethanesulfonic acid
***DTT = dithiothreitol Each apparatus employed to cavitate the protein solution/core material mixture will cause a certain amount of additional heating of the protein solution due to the mechanical shear forces exerted on the solution. That heat must be sufficient to cause localized denaturation of the protein at a gas phase interface. It is thus important to determine the amount of temperature increase caused by the apparatus so that the temperature at which the protein solution is introduced into the apparatus can be adjusted to achieve such local thermal denaturation. Specifically, the bulk temperature of the liquid in the apparatus must coincide with the incipient denaturation temperature immediately prior to cavitation. The cavitation event generates the additional heat necessary to locally denature the protein. Incipient denaturation temperature is defined as the temperature at which the protein is on the verge of denaturation, but the solution does not contain any denatured protein. This temperature is just below, typically 1 to 5° C. below, the denaturation temperature. If necessary, the starting protein solution may be preheated prior to being introduced into the apparatus to a temperature that allows the incipient denaturation temperature to be reached.

Once the proper starting temperature of the protein solution has been achieved, the solution is combined with the gas phase, for example by introducing the gas phase into the protein solution prior to or directly into the cavitation process at a volume to volume ratio in the range of about 1:20 to 2:1 gas phase:liquid, preferably about 1:5 to 1:1. The proper gas phase:liquid ratio will depend on the geometry of the apparatus, and can be adjusted to optimize output.

The gas phase and protein solution are combined and subjected to cavitation under conditions that produce microspheres. This is accomplished using an apparatus in which mechanical shearing and hydrodynamic cavitation can be produced, such as high speed mixers, mills, fluidizers and the like. A preferred apparatus is a colloid mill.

Examples of specific milling apparatus which can be used are as follows:

Model #2½ (Bematek, Beverly, Mass.)

Model W250V (Greerco, Hudson, N.H.)

Model 2F (APV Gaulin, Everett, Mass.)

Model L4R (Silverson, Chesham, UK)

Model Polytron PT3000 (Kinematica, Littaw, Switzerland)

When using a colloid mill, the rotor speed, gap size and gas phase:liquid ratio are the principal process parameters which affect the characteristics (mean size, size distribution, and concentration of microspheres) of the product. Those parameters are adjusted empirically to provide a product having the desired characteristics.

After passing through the mill, the product is cooled, typically to 15–18° C. The cooling step results in condensation of a portion of the perfluoroalkane vapor into the microsphere shell. The resulting microspheres may be sized using a particle counter such as a Coulter Multisizer II particle counter.

The method of the present invention is useful for conventional ultrasound imaging of body tissues or organs such as the heart, liver, kidney, and brain. More particularly, it is useful for imaging tissues or organs, such myocardial tissue, via vascular perfusion of the microspheres. For myocardial imaging (as well as organ perfusion in general), the ultrasound examination is initiated before administration of the microsphere suspensions, and continued during and after administration, and until the image intensity in the myocardial tissue returns to pre-administration "baseline" intensity. The period of time during which the image intensity of the tissue increases is sometimes referred to as "wash-in", and the period of time from when the image intensity of the tissue has peaked until such time that it returns to baseline is referred to as "wash-out." The characteristics of the ultrasonic image during wash-in and wash-out (such as peak intensity level and time necessary to reach peak intensity) can be related to pathological conditions in the tissues and organs being examined.

For use in conventional ultrasound imaging, the suspension of microspheres is injected into a peripheral vein, either as a bolus or continuously infused over a period of time, such as one to ten minutes, at about 0.005 to 0.1 cc per kg body weight. Ultrasonic energy is applied either continuously or intermittently (i.e., pulsed) to the tissue/organ to be imaged, and reflected energy is collected and translated into an image using conventional, commercially available ultrasound imaging equipment.

Two dimensional (2-D) or multidimensional (e.g. three-dimensional (3-D)) echocardiography equipment and procedures may be used to acquire the image. Such procedures and equipment are conventional. Three techniques used to acquire 3-D images are as follows: In the first, a standard transducer is used to collect tomographic images. The transducer is mounted on a track and collects images as it moves along the track. The speed of motion along the track is defined, so that the spacing between tomographic images is known. The collection of slices are then melded together to obtain a 3-D image. In the second, a standard transducer is also used to collect tomographic images. Attached to the transducer is a sensor that is able to report the spatial position of the transducer, so that the relative orientation of various images are known and the images can be melded together to generate a 3-D image. In the third, the transducer consists of a two dimensional array of elements. A one dimensional array of elements is able to acquire a tomographic image; the added dimension allows scanning in the third dimension.

The imaging method of the present invention has been performed in animal models. In these tests, the microspheres used in the imaging method provided excellent backscatter, reduced attenuation, and exhibited longer duration of contrast effects than any of the gas-filled microspheres which were tested.

The invention is further illustrated by the following examples. These examples are not intended to limit the invention in any manner.

EXAMPLES

Example 1

Preparation of Microspheres

Colloid milling produces albumin microspheres by the process of mechanical cavitation. The Gaulin mill uses a 2" flat disc rotating at 20,000 rpm. The gap between the rotor and stator is fixed at 0.0017". A 5% human serum albumin solution for injection is diluted to 1% with USP saline for injection and pumped at 300 mL/min through a ¼" stainless steel coil immersed in a 60° C. thermostated water bath. The warmed albumin solution enters the mill head via a dedicated port.

All gas and vapor supply lines are thermoregulated stainless steel. Pure air (or another suitable gas) from a high pressure cylinder is delivered to the mill through a dedicated port. Air is regulated to 30 psi, with a flow rate of 100 cc /min which is monitored by a calibrated mass/flow meter. Liquid perfluoropentane (300 mL) is poured into a small steel cylinder fitted with a valve, and placed in a hot water bath (92° C.). Perfluoropentane vapor is regulated to 30 psi and directed through a second calibrated mass/flow meter at 100 cc /min (1 g/min). Perfluoropentane vapor combines with the air flow at a "T". The vapor and air are mixed by passage through a thermoregulated 9" static gas mixer just upstream of the mill head. A thermocouple monitors the temperature of the gas/vapor mixture, which is maintained at 70–90° C.

The liquid and gaseous phases combine in the mill at a process temperature of 76.5°±1° C. Microspheres are formed by mechanical cavitation in a suspension of 1% albumin solution. The product is cooled instantly by passage through an inline chiller to 15°–18° C. The product emerges from the chiller into a glass vessel or collection bag. The bulk liquid suspension is stored overnight under refrigeration, resuspended by agitation and filled into individual glass vials or syringes. The product segregates upon standing into a dense white floating layer and a clear undernate. Microspheres made according to this process have a concentration of $4–9 \times 10^8$/mL with a mean size of 4–7 microns, and a total gas volume of 70–200 mL/mL of suspension. Gas chromatography data indicates a perfluoropentane content of approximately 0.5 mg/mL.

Example 2

Pressure Stability of Microspheres

Microspheres from 10 separate lots prepared according to Example 1 using perfluoropentane vapor and air as the gas phase over a range of different ratios were diluted into aerated phosphate buffer saline (PBS) to give a suspension with an optical density of 1 at 600 nm. This corresponds to approximately $1 \times 10^7$ microspheres/mL. The suspension was placed in a pressure cuvette and the optical density monitored as a function of time over 1 minute. Ambient pressure was applied for the first 15 seconds, followed by 10 psi for the next 15 seconds. Pressure was released and returned to ambient for the final 30 seconds.

Figure 1:
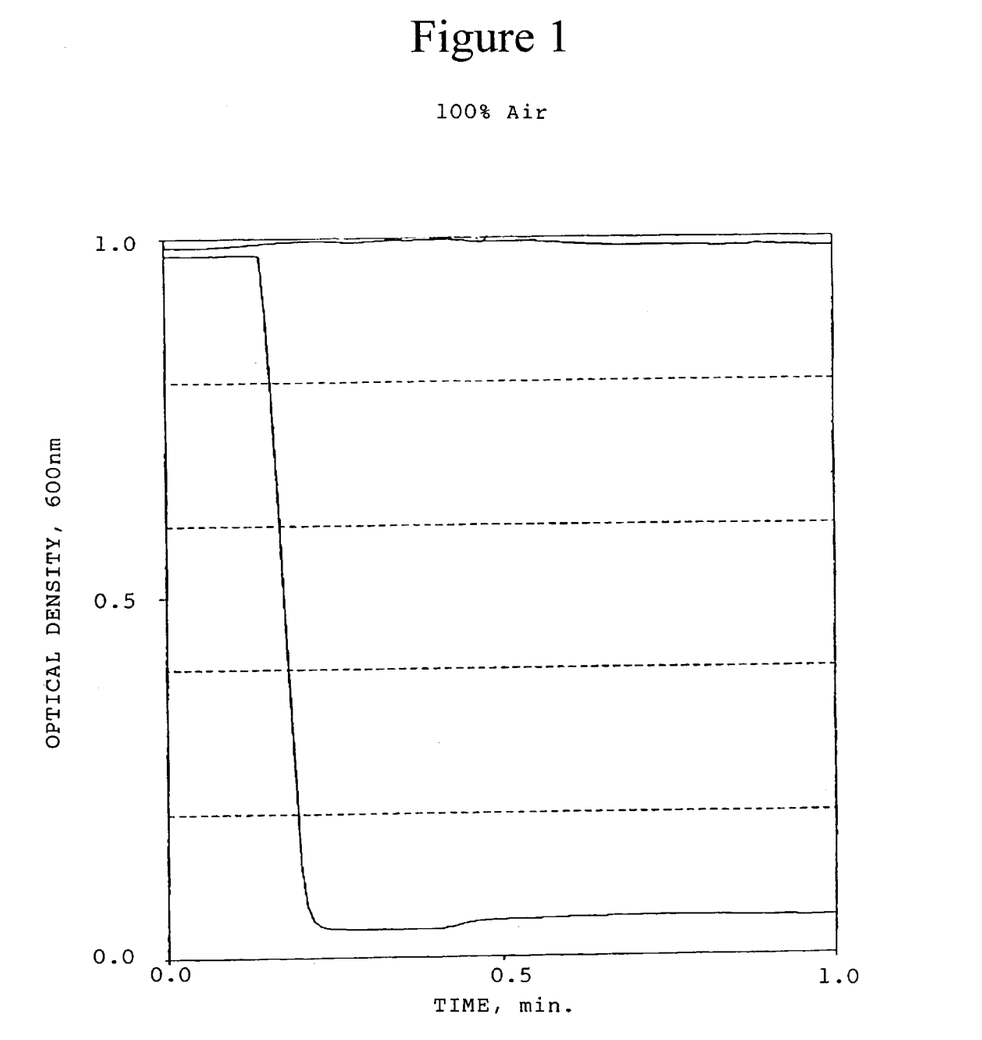
FIG. 1 illustrates the change in optical density at 600 nm upon application of 10 psi pressure of a suspension of microspheres with 100% air as the gas phase.
Figure 2:
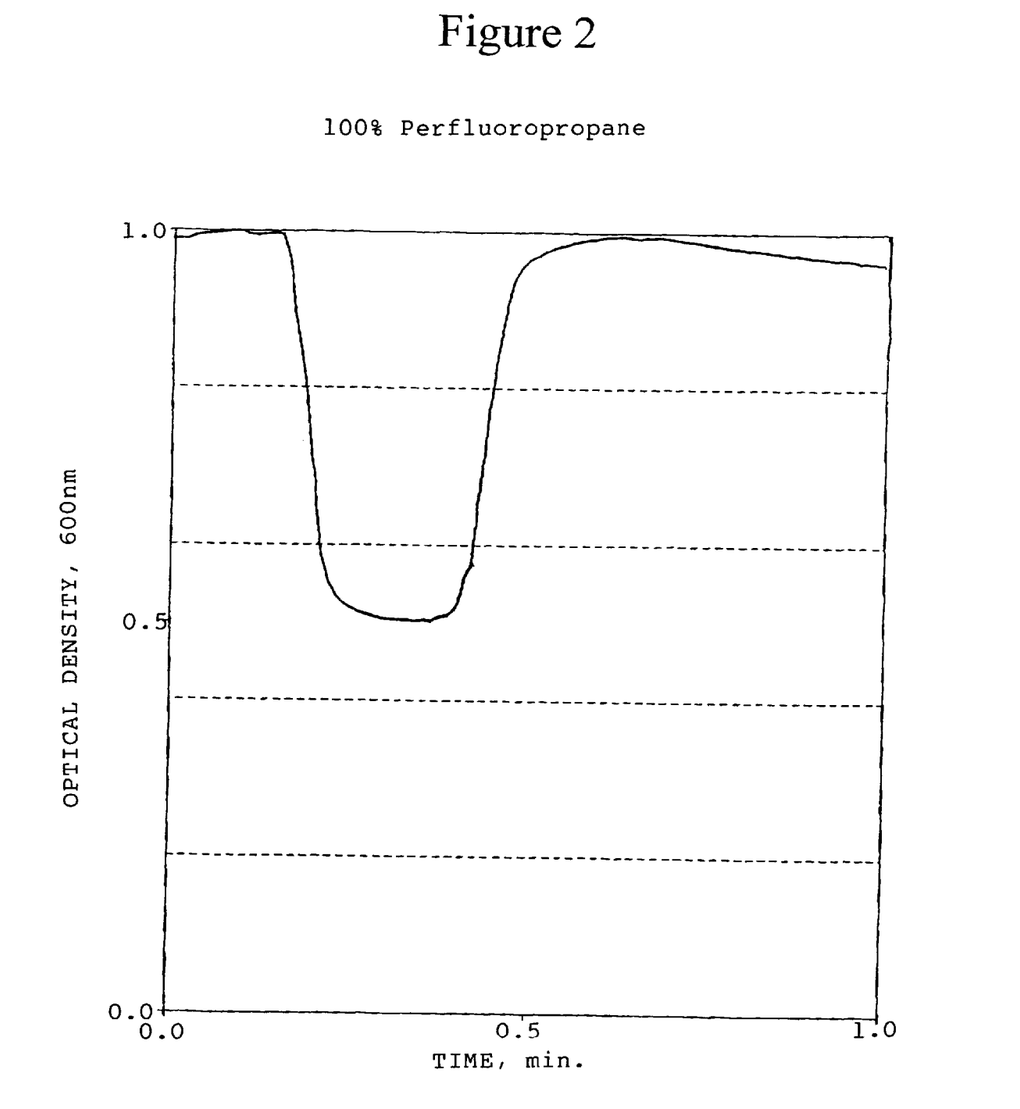
FIG. 2 illustrates the change in optical density at 600 nm upon application of 10 psi pressure of a suspension of microspheres with 100% perfluoropropane as the gas phase.
Figure 3:
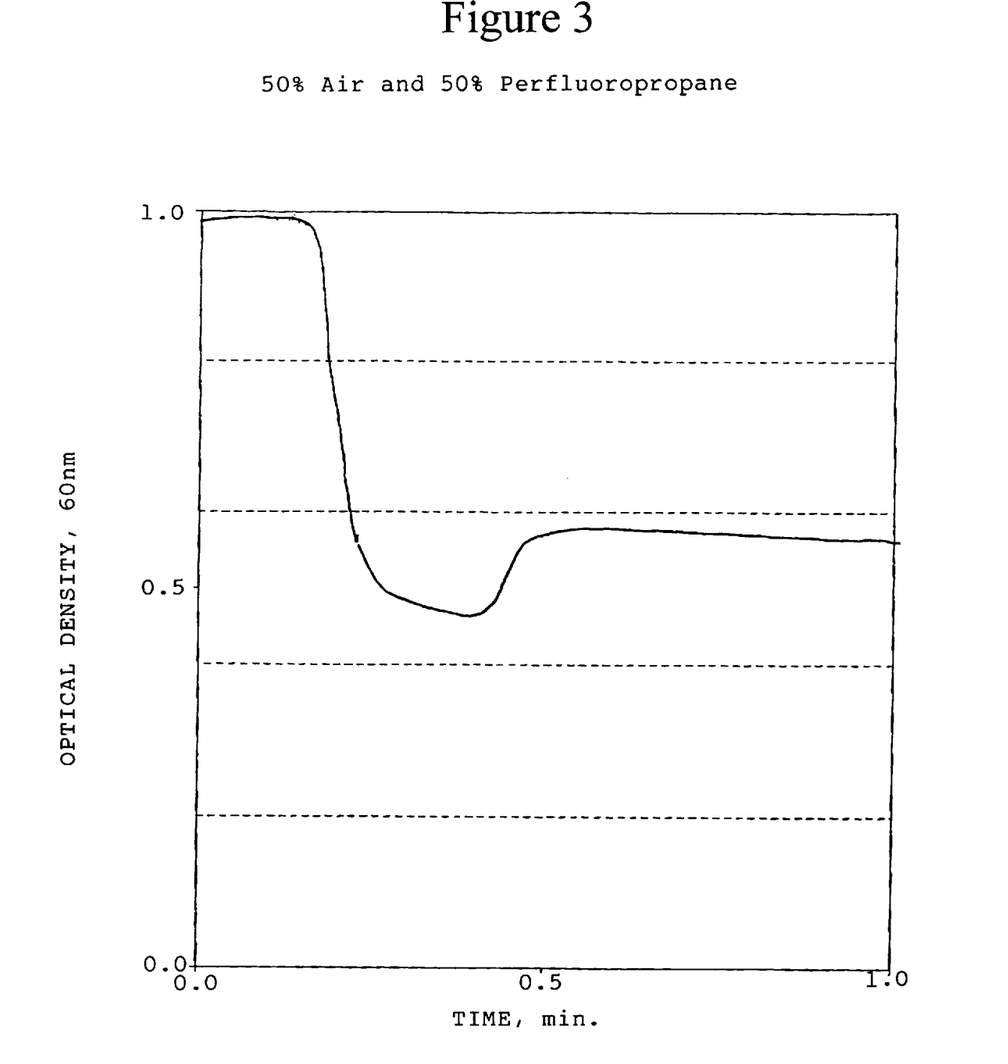
FIG. 3 illustrates the change in optical density at 600 nm upon application of 10 psi pressure of a suspension of microspheres with 50% air and 50% perfluoropane as the gas phase.

The application of pressure causes an increase in solubility of the gas core according to Henry's Law. Air, being much more soluble than perfluoropentane, is driven into solution considerably more effectively by the application of pressure. 100% air filled microspheres (ALBUNEX®, Molecular Biosystems, Inc., San Diego, Calif.), for example, are totally destroyed at $1 \times 10^7$ /mL by 10 psi (FIG. 1). Microspheres filled with 100% perfluoropropane exhibit compression upon application of 10 psi, but recover to the original optical density upon release of pressure (FIG. 2). Microspheres prepared with 50% air and 50% perfluoropropane as the gas phase exhibit compression and incomplete recovery upon the release of pressure (FIG. 3). The air fraction readily dissolves into the surrounding solution and does not reenter upon the release of pressure. The degree of recovery of these microspheres is inversely proportional to the fraction of air present.

Figure 4:
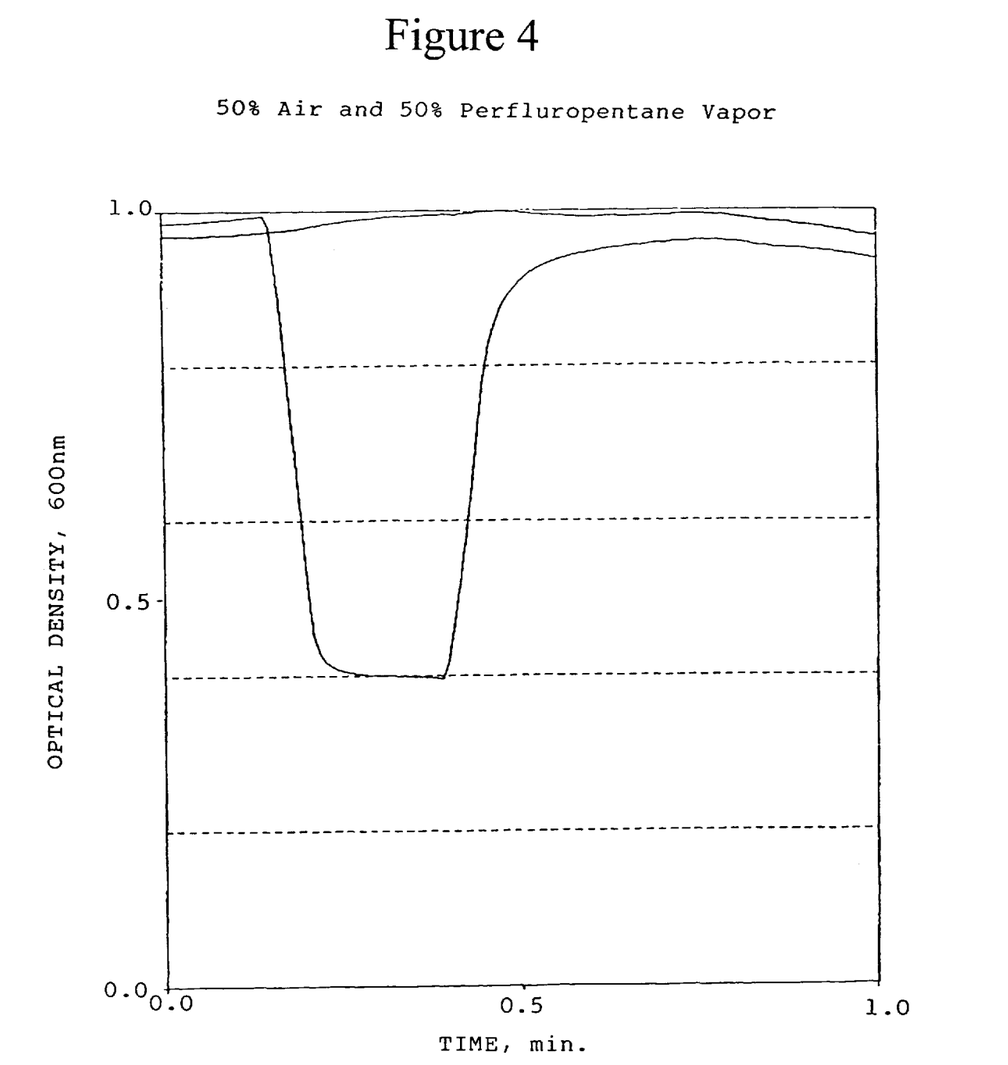
FIG. 4 illustrates the change in optical density at 600 nm upon application of 10 psi pressure of a suspension of albumin microspheres with 50% air and 50% perfluoropentane vapor as the gas phase.
Figure 5:
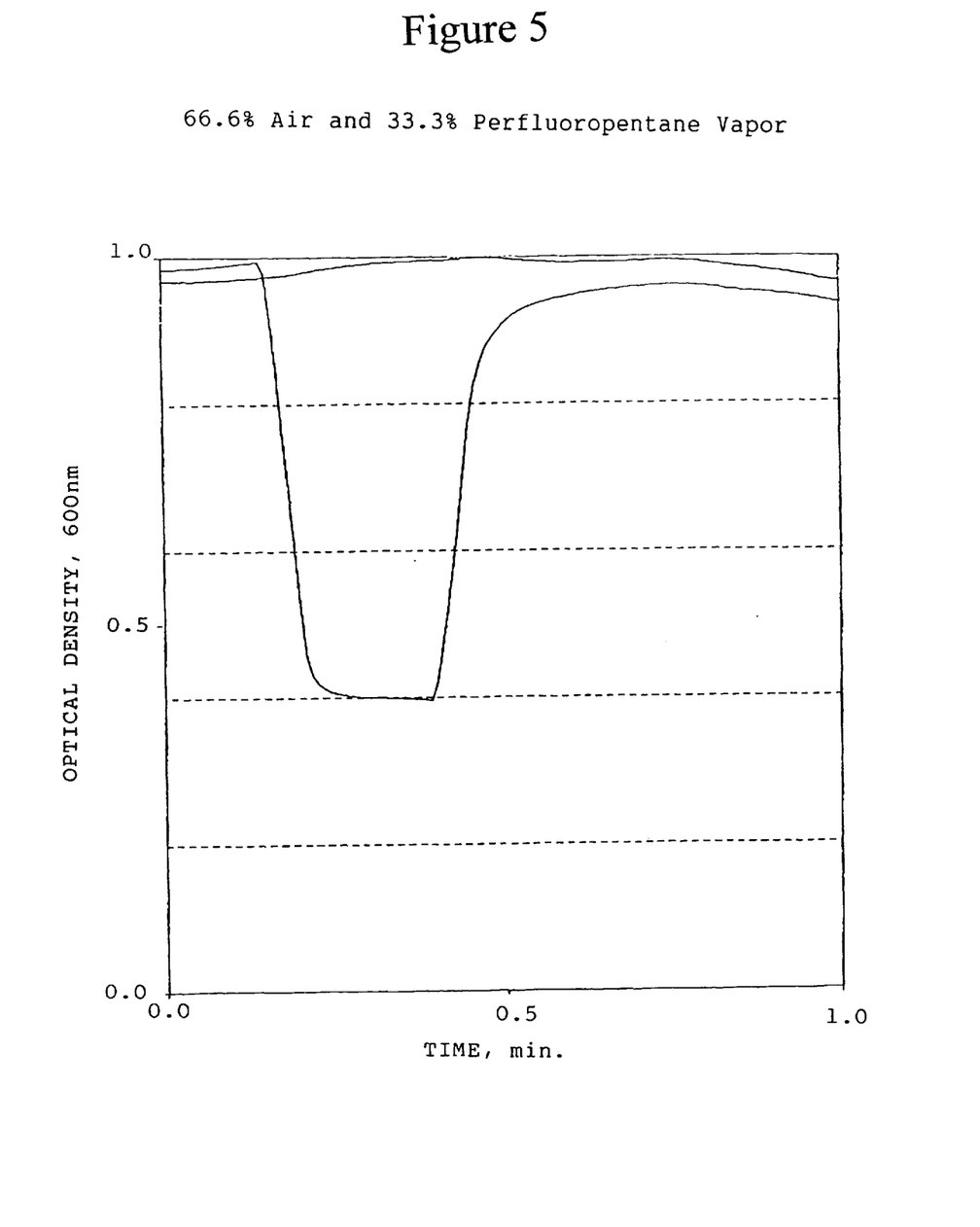
FIG. 5 illustrates the change in optical density at 600 nm upon application of 10 psi pressure of a suspension of albumin microspheres with 66.6% air and 33.3% perfluoropentane vapor as the gas phase.
Figure 6:
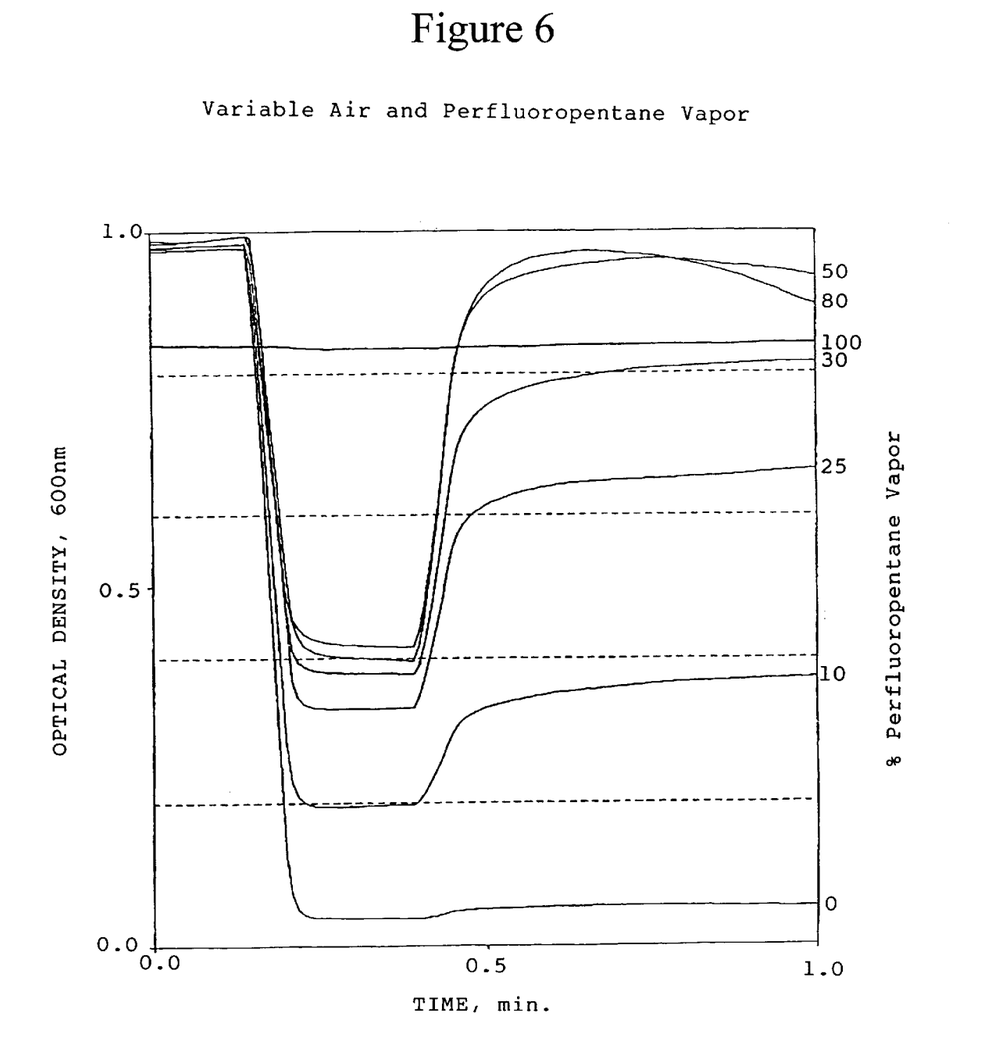
FIG. 6 illustrates the change in optical density at 600 nm upon application of 10 psi pressure of a suspension of albumin microspheres prepared with variable amounts of air and perfluoropentane vapor as the gas phase.

Microspheres prepared according to Example 1 with 50% perfluoropentane vapor and 50% air as the gas phase, and pressure resistance was determined as described above. These microspheres unexpectedly exhibited nearly complete recovery after being subjected to 10 psi. (FIG. 4). Preparations with higher percentages of air also exhibit pressure resistance to a greater degree than expected. FIG. 5 shows the effect of 10 psi on a sample of air: perfluoropentane vapor microspheres prepared with 66% air in the gas phase. These microsphere preparations exhibit almost full pressure resistance. As the air fraction increases, pressure resistance decreases, but the presence of greater than 20% perfluoropentane vapor enhances pressure resistance beyond expectations. FIG. 6 shows the effect of pressure on a range of preparations: 0%, 10%, 25%, 34%, 50%, 80% and 100% perfluoropentane vapor. Microspheres prepared with 100% perfluoropentane vapor are negatively buoyant and are unaffected by the application or the release of 10 psi pressure, i.e., the optical density remains unchanged. This would be expected for a liquid core as liquids are largely incompressible.

Example 3

In Vivo Use of Microspheres for Left Ventricular Opacification

One mL of a microsphere suspension prepared as described in Example 1 (50% perfluoropentane vapor and 50% air as the gas phase) was injected into a 23 kg male, purpose bred canine mongrel. The injection was made via femoral vein catheter followed by a 4–6 mL saline flush. The agent produced complete left ventricular opacification with a peak change in image brightness of 15.8 dB. This agent also enhanced the septum and the posterior wall myocardium with a peak change from baseline of 1.0 and 0.8 dB, respectively. At 2 minutes post injection, the left ventricular chamber remained 1.7 dB above baseline, and 100% filled. The posterior wall myocardium was 0.8 dB above baseline, and in the septum 3.9 dB above baseline. By 4 minutes, both the chamber and septum image intensities had returned to baseline, but the posterior wall remained at 0.2 dB above baseline. This dosage of the agent caused no significant change in hemodynamics. There was no change in the mean arterial pressure and no change in the heart rate. There were also no significant changes in arterial blood gases or pH. Opacification of the left ventricle was observed for at least 4 minutes after injection. At 1.5 minutes post injection, the myocardium remained opacified even though the opacification level in the heart chamber had returned to baseline.

Example 4

In Vivo Imaging Effects of the Myocardium

Microsphere suspensions prepared according to Example 1 exhibit strong and persistent ultrasound contrast in vivo when observed by standard B-mode (fundamental) imaging of the heart. Any cardiac ultrasound view may be used, but the parasternal short axis view allows roughly a midpoint cross sectional viewing plane. Before administration, the left ventricular chamber appears as a dark grey roughly circular structure and the right ventricular chamber is a dark crescent structure. Upon intravenous injection of 0.5 cc of a microsphere suspension made according to Example 1 (50% air and 50% perfluoropentane vapor as the gas phase, with a mean diameter of 5 microns) into an anesthetized canine, the microspheres first (within a few seconds) appear in the right ventricular chamber of the heart. The image of the right ventricular chamber appears bright white followed by a diffuse black shadow (attenuation), except for a bright white margin at the top of the crescent shape, which is proximal to the ultrasound source. Within several heartbeats, white material appears to swirl into the left ventricular chamber, filling it completely, then producing more shadowing in the lower portion of the cardiac image. The microspheres proceed to substantially lighten the grey color of the myocardium as they fill the myocardial vasculature from the coronary arteries. The increased brightness can only be seen at this stage in the areas of the heart tissue most proximal to the ultrasound source because of continued attenuation (shadowing) from the ventricular chamber. The shadowing from the chamber lasts for several seconds, leaving the ventricle a very light grey. At this stage, the myocardium is observed to be similar in intensity and a much lighter shade of grey than the preinjection image.

The microspheres empty first from the right ventricular chamber, then the left ventricular chamber, in time returning the ventricular chambers to baseline image intensity. Approximately 3 to 5 minutes post injection, the left ventricular chamber appears as a dark grey circle surrounded by a bright grey "doughnut shaped" myocardium, indicating the persistence of microspheres in the vasculature of the heart tissue. The brightened myocardium fades slowly with time, returning to baseline intensity in approximately 20 to 30 minutes. Repeat injections produce the same results with no observed adverse effects on heart rate, systemic blood pressure and arterial blood gas levels.

Example 5

In Vivo Organ Perfusion

Using a 5 MHz phased array transducer on a Hewlett Packard Sonos 1500 instrument, transthoracic, parasternal short axis views of the heart in 3 rats, 1 rabbit and 2 canines was visually assessed using conventional ultrasonography after intravenous injection of microsphere suspensions prepared as described in Example 1. These suspensions produced prolonged brightening of the rabbit and rat myocardium (0.01 to 0.1 mL), canine myocardium (0.5 mL), canine kidney and liver (3.0 mL), which followed 1–3 heart beats of far field acoustic attenuation. When assessed by acoustic densitometry, peak brightening of the myocardium showed changes in intensity of 7 to 8 dB in canine myocardium, 2.6 dB in rabbit and 5 to 6.4 dB in rat myocardium. Myocardial brightening persisted after the ventricular chambers had cleared. This image can be likened to that of a doughnut, with the washed-out left chamber in the center surrounded by the brightened myocardium. The visual brightening of the myocardium persisted for approximately 20 to 30 minutes post injections in the anesthetized canines, as compared to 0.5 to 2.0 minutes using perfluoropropane filled albumin microspheres made according to U.S. Pat. No. 4,957,656.

Physiological parameters measured in the in vivo screening of test microsphere suspensions were heart rate and mean arterial pressure. There were no physiologically relevant changes (no more than 5 beats/min or 5 mmHg) after administration of the microsphere suspensions to the animal subjects. No changes in heart rate or mean arterial pressure, nor changes in arterial blood oxygenation, as measured by a clinical peripheral oximeter, have been observed using these microsphere suspensions.

Example 6

Acoustic Properties

Microbubble type contrast agents provide acoustic backscatter and attenuation because of the compressibility of gas. These properties are modified, however, by the presence of a solid shell encapsulating the gas. Differences in the gas in the interior of the microsphere should have little effect upon the acoustic properties, because there is little difference in the compressibility of various gases. In order to determine whether the presence of perfluoropropane vapor during microsphere formation affected the physical properties of the microsphere shell, the acoustic backscatter and attenuation of a microsphere suspension prepared as described in Example 1 ("test" microspheres) was measured and compared to perfluoropropane filled albumin microspheres prepared according to U.S. Pat. No. 4,957,656 ("control" microspheres), and with ALBUNEX® (air-filled albumin microspheres, Molecular Biosystems, Inc., San Diego, Calif.)

A small amount of sample, 13 $\mu$l–25 $\mu$l, was added to a cylindrical sample chamber filled with 62 ml of Isoton®II. The sample chamber was placed within a temperature controlled water bath and rotated at 25 rpm to keep the microsphere suspension homogeneous. Either one of two Panametrics ultrasonic transducers (center frequency=2.25 MHz or 5.0 MHz) were excited by a Panametrics Model 5800-101 Pulser/Receiver to emit an ultrasound burst. The backscattered ultrasound was received by the transducer, detected by the Pulser/Receiver and digitized by a Hewlett Packard Model 54505B digital oscilloscope. The data acquisition process was controlled by a personal computer. Approximately 50 backscatter measurements were made upon each sample, and multiple samples were tested from each lot The data analysis included calculating the logarithm of the integrated backscattered power as a function of the depth within the sample chamber. A linear regression was performed on the data at each frequency, with the y-intercept proportional to the scattering strength, and the magnitude of the slope proportional to the attenuation for the test microspheres. The correlation coefficient was 0.998 at 2.5 MHz, and 0.994 at 5.0 MHz.

The acoustic backscatter and attenuation of the test and control microsphere suspensions were calculated. These calculations incorporated the size distribution and concentration of the microsphere suspensions, so that comparisons of the acoustic properties may be made which are independent of the microsphere size and concentration. The calculations were made using the theory described by C. Church (J. Acoust. Soc. Amer., 97(3) 1510–1521 (1995).) The calculations were based on the incident ultrasound frequencies, the temperature of the water bath, the dilution, and the size distributions and concentrations of the microsphere suspensions which were measured using a Coulter® Multisizer particle analyzer.

For attenuation and backscatter at the two ultrasound frequencies, the correlation coefficient of the measurements and the calculations for multiple lots of control microsphere suspensions ranged from 0.79 to 0.98. This linear relationship demonstrated the appropriateness of the theory. The 95% prediction interval of this line was determined for attenuation and backscatter at 2.25 MHz and 5.0 MHz. The data points for the calculations and measurements of backscatter of the test microsphere suspensions fall outside the prediction interval at both ultrasound frequencies. Data points for the calculations and measurements of attenuation at 2.25 MHz of the test microsphere suspensions also fell outside the prediction interval. The scattering strength and attenuation of this formulation is statistically significantly less than that of the control microspheres with an equivalent size distribution.

Therefore, the observed differences in the acoustic properties of the test microspheres compared to those of the control microspheres are attributable to differences in properties of the shell, such as thickness, viscosity, and/or rigidity.

Example 7

Comparison of Conventional Imaging v. Harmonic Imaging

Suspensions of microspheres made according to Example 1 with 50% perfluoropentane vapor and 50% air as the gas phase ("test" microspheres) were compared to suspensions of perfluoropropane filled albumin microspheres made according to U.S. Pat. No. 4,957,656 ("control" microspheres) using both conventional ultrasonic imaging and harmonic imaging.

A canine myocardium was imaged as described in Example 3 after injection of equivalent doses of test microspheres with conventional ultrasound imaging and with harmonic imaging. Images were obtained before and after administration of the test microsphere suspension. A region of interest ("ROI") within the myocardium was chosen, and the image intensity within this ROI was determined. The post-administration image intensity in the ROI after subtracting the pre-administration baseline intensity was 29 grey scale units, indicating that the conventional image was enhanced after administration of the test microsphere suspension. This experiment was repeated using harmonic imaging. No enhancement of the image intensity was observed after administration of the test microsphere suspension, i.e. the image intensity did not increase above the pre-administration baseline intensity.

This experiment demonstrates that the test microspheres do not exhibit resonant properties that can be exploited using harmonic imaging. In comparison, control microsphere suspensions have been reported to exhibit image enhancement using harmonic imaging. See, for example Dittrich, et al. (Abstract submitted to the American College of Cardiology, 45th Annual Scientific Session, 1996), who reported that perfluoropropane-filled albumin microspheres enhanced harmonic images of the myocardium.

Modifications of the above-described modes for carrying out the invention that are obvious to persons of skill in the field of ultrasound contrast agents are intended to be within the scope of the following claims. All publications, patents, and patent applications cited in this specification are incorporated herein by reference as if each such publication, patent or patent application were specifically and individually indicated to be incorporated herein by reference.

We claim:

1. A method of imaging a tissue or organ of a subject comprising the steps of:
   (a) administering to said subject a suspension of microspheres comprising a gas core encapsulated by a shell of heat-insolubilized protein, wherein said microspheres are formed by contacting a heat-insolubilizable protein with a gas phase comprising a gas and a heated perfluoroalkane vapor;
   (b) waiting for a sufficient length of time for said microspheres to reach said tissue or organ and perfuse therein;
   (c) applying ultrasonic energy to said subject; and
   (d) generating an ultrasonic image from said ultrasonic energy reflected from said tissue or organ.

2. The method of claim 1 wherein said tissue or organ is a heart having a myocardium and a left and right ventricular cavity, and step (b) further comprises waiting for a sufficient length of time for said microspheres to reach said heart, fill said left ventricular cavity, perfuse said myocardium, exit said left ventricular cavity, and exit said myocardium.

3. The method of claim 1 wherein said gas has a solubility greater than or equal to 0.01 mL of gas per mL of water at 25° C. at 1 atmosphere pressure.

4. The method of claim 3 wherein said gas is air.

5. The method of claim 1 wherein said perfluoroalkane vapor is perfluoropentane vapor.

6. The method of claim 5 wherein said protein is albumin.

7. The method of claim 5 wherein said perfluoropentane vapor is between about 20% to 50% (v/v) of said gas phase.

8. The method of claim 7 wherein said perfluoropentane vapor is 50% of said gas phase and said protein is albumin.

9. The method of claim 8 wherein said gas is air.

10. The method of claim 1 wherein said perfluoroalkane vapor is perfluorohexane vapor.

11. The method of claim 10 wherein said protein is albumin.

12. The method of claim 10 wherein said perfluorohexane vapor is between about 10% to 20% (v/v) of said gas phase.

13. The method of claim 1 wherein said perfluoroalkane vapor is perfluoroheptane vapor.

14. The method of claim 13 wherein said protein is albumin.

15. The method of claim 13 wherein said perfluoroheptane vapor is between about 7% to 15% of said gas phase.

16. The method of claim 1 wherein said microspheres are present in said suspension in a concentration of between $1 \times 10^7$ to $1 \times 10^{10}$ microspheres per mL of suspension.

17. The method of claim 1 wherein said microsphere suspension is administered intravenously as a bolus injection.

18. The method of claim 1 wherein said microsphere suspension is administered intravenously over a period of at least 1 minute.

19. The method of claim 1 wherein step (d) further comprises generating a two-dimensional ultrasonic image.

20. The method of claim 1 wherein step (d) further comprises generating a three-dimensional ultrasonic image.

21. The method of claim 1 wherein step (c) further comprises applying continuous ultrasonic energy.

22. The method of claim 1 wherein step (c) further comprises applying pulsed ultrasonic energy.

23. The method of claim 1 wherein step (a) further comprises administering said microsphere suspension from a pre-filled syringe.

24. The method of claim 1 wherein said gas has a solubility less than 0.01 mL per mL of water at 25° C. and 1 atmosphere pressure.

25. The method of claim 24 wherein said gas is perfluoropropane.

26. A process for making microspheres useful as ultrasonic imaging agents having a gas core encapsulated by a shell of a heat-insolubilized protein comprising the steps of:

(a) mixing a gas phase comprising a gas and perfluoroalkane vapor which has been heated to a temperature above its boiling point and close to the denaturation temperature of the protein with a solution of a heat-insolubilizable protein;

(b) cavitating said mixture under conditions which form microspheres by heat-insolubilizing said protein; and (c) cooling said microspheres to condense at least a portion of said perfluoroalkane into said shell.

27. The process of claim 26 wherein said gas has a solubility greater than or equal to 0.01 mL per mL of water at 25° C. at 1 atmosphere pressure.

28. The process of claim 27 wherein said gas is air.

29. The process of claim 26 wherein said protein is albumin.

30. The process of claim 26 wherein said perfluoroalkane vapor is perfluoropentane vapor.

31. The process of claim 30 wherein said perfluoropentane vapor is between about 20% to 50% (v/v) of said gas phase.

32. The process of claim 30 wherein said perfluoropentane vapor is 50% of said gas phase and said protein is albumin.

33. The process of claim 32 wherein said gas is air.

34. The process of claim 26 wherein said perfluoroalkane vapor is perfluorohexane vapor.

35. The process of claim 34 wherein said perfluorohexane vapor is between about 10% to 20% (v/v) of said gas phase.

36. The process of claim 26 wherein said perfluoroalkane vapor is perfluoroheptane vapor.

37. The process of claim 36 wherein said perfluoroheptane vapor is between about 7% to 15% of said gas phase.

38. The process of claim 29 wherein said albumin is present in said solution of said protein at a concentration of 1% to 5% by weight, inclusive.

39. The process of claim 26 wherein said cavitation occurs by applying ultrasonic energy.

40. The process of claim 26 wherein said cavitation occurs by applying mechanical energy.

41. A composition for use as an ultrasound imaging agent comprising a suspension of microspheres, said microspheres comprising a gas core encapsulated by a protein shell, wherein said microspheres are formed in the presence of a gas phase comprising a gas and a heated perfluoroalkane vapor.

42. The composition of claim 41 wherein said gas has a solubility greater than or equal to 0.01 mL of gas per mL of water at 25° C. at 1 atmosphere pressure.

43. The composition of claim 41 wherein said gas is air.

44. The composition of claim 41 wherein said protein is albumin.

45. The composition of claim 41 wherein said perfluoroalkane vapor is perfluoropentane vapor.

46. The composition of claim 45 wherein said perfluoropentane vapor is between 20% to 50% (v/v) of said gas phase.

47. The composition of claim 46 wherein said perfluoropentane vapor is 50% of said gas phase and said protein is albumin.

48. The composition of claim 47 wherein said gas is air.

49. The composition of claim 41 wherein said perfluoroalkane vapor is perfluorohexane vapor.

50. The composition of claim 49 wherein said perfluorohexane vapor is between about 10% to 20% (v/v) of said gas phase.

51. The composition of claim 41 wherein said perfluoroalkane vapor is perfluoroheptane vapor.

52. The composition of claim 51 wherein said perfluoroheptane vapor is between about 7% to 15% of said gas phase.

53. The composition of claim 41 wherein said microspheres exhibit pressure resistance at 10 psi.

54. The composition of claim 44 wherein said albumin is human serum albumin.

55. The composition of claim 41 wherein said microspheres have a mean diameter in the range of 0.1 and 10 microns.

56. The composition of claim 41 wherein said microspheres are present in said suspension at a concentration of from $1 \times 10^7$ to $1 \times 10^{10}$ microspheres per mL of suspension.

57. The composition of claim 41 wherein said microspheres have a mean diameter in the range of 1 to 5 microns.

58. The composition of claim 41 wherein said shell is modified to include moieties that target a specific tissue or organ.

59. A composition for use as an ultrasound imaging agent comprising a suspension of microspheres, said microspheres comprising a gas phase of 50% gas and 50% perfluoropentane (v/v) encapsulated by a shell of heat-insolubilized protein.

60. The composition of claim 59 wherein said gas is air.

* * * * *